United States Patent [19]
Bier et al.

[11] Patent Number: 5,447,612
[45] Date of Patent: Sep. 5, 1995

[54] BUFFERING SYSTEM AND ITS USE IN ELECTROPHORETIC PROCESSES

[75] Inventors: Milan Bier; Terry D. Long; Rodolfo B. Marguez; James A. Ostrem, all of Tucson, Ariz.

[73] Assignee: Protein Technologies, Inc., Tucson, Ariz.

[21] Appl. No.: 363,640

[22] Filed: Dec. 22, 1994

Related U.S. Application Data

[63] Continuation of Ser. No. 148,638, Nov. 4, 1993, abandoned, which is a continuation-in-part of Ser. No. 11,887, Feb. 1, 1993, abandoned.

[51] Int. Cl.$^6$ ............................................. C25B 7/00
[52] U.S. Cl. ........................... 204/182.8; 204/299 R; 204/182.9; 204/183.2
[58] Field of Search ............. 204/182.8, 299 R, 182.9, 204/183.2

Primary Examiner—Kathryn Gorgos
Assistant Examiner—C. Delacroix Muircheid
Attorney, Agent, or Firm—Ogram & Teplitz

[57] ABSTRACT

A novel pH buffering system which is functionally stable under electrophoretic conditions employs buffering components in complementary buffer pairs. The buffering components are selected from among simple chemically defined ampholytes, weak acids and weak bases, and are paired together on the basis of their dissociation characteristics to define narrow overlapping buffering zones in which the buffering components exhibit low net electrophoretic mobility combined with desired pH buffering capacity. The narrow buffering zones cover from 0.4 to 1.25 pH units within a broad range of pH values of from about pH 3 to about pH 10. Specific buffering pH values within the narrow buffering zones are obtainable by varying the molar ratios of the two buffering components of the selected buffer pair. The buffering system may be used to form functionally stable precast narrow pH zone gradients in free solution, and has particular utility in isoelectric focusing and other electrophoretic processes.

52 Claims, 2 Drawing Sheets

BUFFERING SYSTEM AND ITS USE IN ELECTROPHORETIC PROCESSES

This is a continuation of application Ser. No. 08/148,638, filed Nov. 4, 1993, now abandoned which in turn is a continuation-in-part of application Ser. No. 08/011,887, filed Feb. 1, 1993, now abandoned.

BACKGROUND OF THE INVENTION

This invention relates to buffering systems for controlling the pH of aqueous media and, more particularly, to pH buffering systems useful in isoelectric focusing and in other electrophoretic processes.

Effectively controlling the pH of aqueous media with suitable biologically acceptable buffers is essential for much of biochemistry and microbiology, as well as other life sciences. It is essential for such biological techniques as, for example, protein extraction, preservation and purification, chromatography and HPLC, enzyme assays and reactions, tissue culture, organ preservation and perfusion, and electrophoresis. Electrophoretic processes present special buffering problems, since the buffering system must be functionally stable under the influence of an electric field. This is particularly so in the case of isoelectric focusing ("IEF"), an electrophoretic technique requiring functionally stable pH gradients.

IEF is a high resolution method useful for both analytical and preparative separation and purification of various biological materials, mainly proteins and peptides, but occasionally also nucleic acids, viruses, and even some living cells or cell organelles. The principle of IEF is based on the fact that certain biomaterials are amphoteric in nature, i.e., are positively charged in acidic media and negatively charged in basic media. At a particular pH value, known as the isoelectric point, they undergo a reversal of net charge polarity passing through a point of zero net charge. The isoelectric point of any given amphoteric substance is a characteristic of its chemical composition. When a mixture of such substances is exposed to an applied external d.c. electric field within a pH gradient, each component of the mixture will migrate electrophoretically until it reaches the pH corresponding to its isoelectric point, where it will become virtually immobilized due to having acquired zero net charge. The end result is a steady state in which all components are focused into narrow pH zones corresponding to their respective isoelectric points.

The effectiveness of IEF as a high resolution separation and purification technique depends heavily on the use of buffering systems which are capable of forming pH gradients exhibiting functional stability under electrophoretic conditions. Two distinct approaches have been taken in the prior art in the development of suitable buffering systems for forming functionally-stable pH gradients. These two approaches differ in the manner in which the pH gradient is generated. In one approach, known as "natural" pH gradients, the pH gradient is generated within the focusing system by the electric field itself. In the other approach, known as "precast" pH gradients, the pH gradient is preformed or precast in the system and not generated by the electric current.

The formation of natural pH gradients relies on buffering systems composed of ampholytes having sharply defined isoelectric points. The theory of this approach is that in an electric field, each ampholyte will migrate electrophoretically towards its isoelectric point, modifying at the same time the local pH. Finally, a steady state will be achieved where all ampholytes have migrated to their isoelectric points, thereby establishing a pH gradient. An ampholyte's ability to focus sharply to its isoelectric point and to effectively control the pH is related to its pK spread, i.e., the spread between its acidic function dissociation constant $pK_1$ and its basic function dissociation constant $pK_2$ which are proximal to its isoelectric point pI, the pI being the algebraic midpoint of the spread.

Svensson (Acta Chem. Scand. Vol. 15, pp. 325-341, 1961) was the first to propose this method of gradient formation, but concluded that only ampholytes with a pK spread of less than 3-4 pH units are "good" for this purpose. Unfortunately, most simple ampholytes, such as amino acids and their derivatives, have larger pK spreads and are unusable for formation of natural pH gradients, having neither sufficient buffering power nor electrical conductivity when focused. Consequently, ampholytes having a pK spread of greater than 4 pH units have not previously been found suitable for use in pH gradient formation, thereby eliminating most of the simple ampholytes of known chemical composition. This includes also the so-called Good's buffers (described more fully in Good et al., Biochemistry Vol. 5, p.467, 1966 and Ferguson and Good, Anal. Biochem. Vol. 104, p. 300, 1980) specifically designed for biologically acceptable buffering. Subsequent literature on IEF is too extensive to be cited, but a recent and thorough review of the main electrophoretic methods is to be found in the monograph "The Dynamics of Electrophoresis" by Mosher, Thormann and Saville (VCH Publishers, 1992).

To overcome this obstacle, suitable synthetic buffering mixtures known as carrier ampholytes were formulated as random polymerization products comprising a large number of synthetic polyelectrolytes with a broad range of isoelectric points. Commercially available carrier ampholytes include, for example, those sold under the tradenames "Ampholine", "Pharmalyte", "Servalyte" and "Biolyte". These carrier ampholytes serve well for analytical IEF, since they create stable broad or narrow range pH gradients under electrophoretic conditions, particularly when used in conjunction with stabilizing hydrophilic gel media, such as polyacrylamide or agarose. They are less well suited for preparative IEF, since by the very nature of their synthesis they are chemically ill-defined and thus contaminate the final product. This contamination problem is even further complicated when a gel medium is used for stabilization of the pH gradient. As a result, there have been numerous attempts to formulate natural pH gradient-forming buffer mixtures of known structure. These have included mixtures of ten buffering components, as described by Chrambach et al, U.S. Pat. No. 4,139,440, issued Feb. 13, 1979; and mixtures of at least four buffering components as described by Hearn et al, U.S. Pat. No. 4,279,724, issued Jul. 21, 1981. However, none of these buffer mixtures has proven to be as effective as the carrier ampholytes for forming natural pH gradients over a wide range of pH values.

The second approach to focusing relies on precast pH gradients having the requisite functional stability. This approach has heretofore been limited almost exclusively to employing precast pH gradients wherein the buffering components are immobilized by copolymerization within polyacrylamide gel media or polyacrylamide membranes. Specially formulated copolymerizable buffering agents are commercially available under the tradename "Immobiline", and have been used in the gel-immobilized form primarily for analytical IEF, as well as in the membrane-immobilized form better suited for preparative IEF (cf., for example, Faupel & Righetti, U.S. Pat. No. 4,971,670, issued Nov. 20, 1990.

Thus, until now, the only known effective technique for obtaining gel-free pH gradients useful over a wide range of pH values, has been through natural pH gradient formation, which limits buffering component selection to only those ampholytes which focus sharply to isoelectric points coinciding with the desired buffering pH value. Excluded from this limited selection are most of the simple ampholytes of known chemical composition, which have generally been regarded as unsuitable for use in pH gradient formation.

A number of two-component buffering systems, both real and hypothetical, employing simple ampholytes, weak acids and weak bases, have been proposed for use in pH gradient formation in a series of papers co-authored by the present inventor. These papers include Palusinski et al, Biophysical Chemistry, vol.13, pp. 193–202, (1981); Bier et al, Journal of Chromatography, vol. 211, pp. 313–335 (1981); Bier et al, Science, vol. 219, pp. 1281–1287 (1983); Bier et al, in: Hirai (Ed.) Electrophoresis '83, de Gruyter, Berlin, pp. 99–107 (1984); Mosher et al, Electrophoresis, vol. 6, pp. 545–551 (1985); and Bier et al, Journal of Chromatography, vol. 604, pp. 73–83 (1992). The buffering systems disclosed in these papers have had only very limited utility, either in purely theoretical applications or in providing buffering in a limited pH range at or near neutrality. Furthermore, these papers fail to establish any criteria for the rational selection of buffering components to provide buffer pairs having practical utility over a wide range of pH values. In fact, out of all the various buffer pairs disclosed in these six papers, only two would actually meet the selection criteria of the present invention. One of these is a hypothetical buffer pair of a first ampholyte whose $pK_2$ is 8.0 and a second ampholyte whose $pK_1$ is 5.0, disclosed in the 1981 Palusinski et al paper (Table 2, System C). The other is the buffer pair of alpha-Asp-His/isoglutamine, disclosed in the 1981 Bier et al paper as the fourteenth of twenty-eight entries in Table II. Moreover, from a reading of these papers, one would not expect either of these two buffer pairs to have any particular utility other than in theoretical studies. In fact, both of these buffer pairs are indicated in the papers as being less desirable than other listed buffer pairs for the purposes described. Thus, the listing of these two buffer pairs would not in any way be suggestive of the selection criteria utilized in carrying out the present invention.

SUMMARY OF THE INVENTION

The present invention is directed to a novel buffering system which is functionally stable under electrophoretic conditions and which uses simple buffering components of known chemical compositions. These components are employed in complementary pairs designed to provide buffering compositions exhibiting desired pH buffering capacity combined with low net electrophoretic mobility of buffering components. Each complementary pair will buffer over only a narrow buffering zone within a broad range of pH values of from about pH 3 to about pH 10. The buffering components are selected from among a wide variety of chemically defined ampholytes, weak acids and weak bases having known characteristic dissociation constants, and are paired together on the basis of these characteristics. These dissociation constants are used to define overlapping buffering zones characterized by having an "electrophoretic reserve capacity" within the range of from at least 0.85 to no more than 0.99, with the bulk of the ionized species being negatively charged for one buffering component and positively charged for the other. A result of this selection process is that the buffering composition can be designed to have satisfactory pH buffering capacity while exhibiting low net electrophoretic mobility of both buffering components.

As used throughout this specification and in the appended claims, the "electrophoretic reserve capacity" of a buffering component is defined as the ratio of the neutral species concentration to the total concentration of a buffering component in a solution of the buffering component. This is a novel notion, essential for the understanding of the invention. A component with a low electrophoretic reserve capacity will be nearly fully ionized and will migrate rapidly in an electric field. Thus, it may cause rapid pH changes within the solution. To the contrary, a component with a high electrophoretic reserve capacity, in the above specified range of at least 0.85, will have but a low net mobility and migrate only slowly. Moreover, any loss of the ionized species will be compensated by the dissociation of the available reserve of the neutral species, thus minimizing change of pH. Components with an electrophoretic reserve capacity of over 0.99 will have insufficient buffering capacity to control the pH and insufficient conductivity to carry the current. It is further understood that for a weak electrolyte or a simple ampholyte the distribution of ionized and neutral species is mainly the function of the pH of the solution.

Because of the logarithmic definition of pH, base 10, the buffering system of the present invention provides pH buffering within narrow buffering zones extending no more than 1.25 pH units. By using a properly selected pair of complementary first and second buffering components having, respectively, first and second operative dissociation constants, the range of from about pH 3 to about pH 10, can be covered. The first buffering component acts as an acidic titrant, and is either a first ampholyte having an isoelectric point pI defined by the proximal dissociation constants $pK_1$ and $PK_2$, or a weak acid having a dissociation constant pK. The first operative dissociation constant of the first buffering component is either the $pK_2$ of the first ampholyte or the pK of the weak acid. These known characteristics of the first buffering component establish a first buffering zone extending below the first operative dissociation constant and within which it exhibits ionization with an electrophoretic reserve capacity of from at least 0.85 to no more than 0.99 and with the bulk of its ionized species being negatively charged. The second buffering component acts as a basic titrant, and is either a second ampholyte having an isoelectric point pI, defined by the proximal dissociation constants $pK_1$ and $pK_2$, wherein this second ampholyte has a higher pI than the first ampholyte, or a weak base having a dissociation constant pK. The second operative dissociation constant of the second buffering component is either the $pK_1$ of the second ampholyte or the pK of the weak base, and is at least 2.4 pH units below the first operative dissociation constant of the first buffering component. These known characteristics of the second buffering component establish a second buffering zone extending above the second operative dissociation constant and within which it exhibits ionization with an electrophoretic reserve capacity of from at least 0.85 to no more than 0.99 and with the bulk of its ionized species being positively charged.

The buffer pair of complementary first and second buffering components must have at least partially overlapping first and second buffering zones covering from 0.4 to 1.25 pH units, wherein the overlapping portions coincide with and define the narrow buffering zone of the buffering composition. Specific buffering pH values within this narrow buffering zone are obtainable by varying the molar ratios of the two buffering components of the selected buffer pair. A molar ratio of the second buffering component to the first buffering component within the range of from about 1:9 to about 9:1 will generally be effective for maintaining the buffering pH value within the narrow buffering zone. Within such range of molar ratios, the specific buffering pH value of the composition will increase in a substantially linear relation with the proportion of the second buffering component.

The buffering system of the present invention may be utilized to provide buffering of aqueous media to within any desired narrow buffering zone covering from 0.4 to 1.25 pH units within a broad range of pH values of from about pH 3 to about pH 10, by proper selection of the buffer pair of complementary first and second buffering components. The buffering zone of the resulting composition coincides with that pH zone encompassed within the buffering zones of both buffering components.

The unique combination of properties exhibited by the buffering system of the present invention, makes it particularly suitable for use in various electrophoretic processes requiring buffers exhibiting functional stability under electrophoretic conditions. Of special significance is its capability of forming functionally stable precast narrow pH zone gradients in free solution for use in IEF. In forming such pH gradients employing the buffering system of the present invention, the proportion of the complementary first and second buffering components will be progressively varied in either substantially continuous or stepwise increments to cover the desired pH zone. Furthermore, because the buffering system of the present invention uses simple buffering components of known chemical composition which can be easily identified and separated from the system, and does not require contaminating gel-immobilization or gel-stabilization for the functional stability of the pH gradient, it is particularly well suited for preparative IEF. Different complementary buffering pair combinations have to be used to cover a wide range of pH values.

It will be understood that the buffering compositions per se having as their buffer pair the specific combination of a first ampholyte whose $pK_2$ is 8.0 and a second ampholyte whose $pK_1$ is 5.0 (as disclosed in the above-referenced 1981 Palusinski et al paper), or the specific buffer pair of alpha-Asp-His/isoglutamine (as disclosed in the above-referenced 1981 Bier et al paper), are not intended to be part of the present invention and are expressly excluded therefrom. Such exclusion is not intended to apply, however, to the selection criteria and methods of use forming part of the present invention and not disclosed or suggested in these two papers.

DESCRIPTION OF PREFERRED EMBODIMENTS

The present invention constitutes an entirely novel approach to the long-standing problem of designing buffering systems using chemically well defined compounds, which possess sufficient functional stability under electrophoretic conditions for use in electrophoretic processes, and in particular, for use in establishing and maintaining the pH gradients required in IEF. The novel approach relies on applying certain basic concepts of acid-base equilibria to define pH zones where buffering components will exhibit a desirable buffering capacity combined with low net electrophoretic mobility of buffering components, and then pairing together complementary buffering components having such pH zones in common. By following this approach, it has been unexpectedly discovered that there is a wide range of simple ampholytes of known chemical composition, previously thought to be totally unusable for pH gradients in IEF due to their poor conductivity and low buffering capacity when focused at their isoelectric points, which are, in fact, usable for that purpose in the buffering system of the present invention. Moreover, since the buffering system of the present invention does not rely upon the focusing of its components, even weak acids and weak bases are usable therein. It has furthermore been unexpectedly discovered that through the use of the buffering system of the present invention, it becomes possible to economically establish functionally stable free solution precast pH gradients suitable for IEF. These unexpected features combine to render the buffering system of the present invention particularly well suited for preparative IEF as the gradient-forming buffering components are chemically defined and biologically acceptable.

The acid-base equilibria concepts forming the basis of the present invention focus on the relationship which exists between the dissociation constants of the buffering components and the desired properties of the buffering system. These desirable properties are: adequate buffering capacity, sufficient electrical conductivity, high electrophoretic reserve capacity, and low net electrophoretic mobility of buffering components.

With respect to buffering capacity, the dissociation constant DK of a simple monovalent buffering component corresponds to the pH at which it has its maximum buffering capacity, and the buffering capacity decreases logarithmically and symmetrically to either side of the pK. The net electrophoretic mobility of a buffering component is the product of its inherent mobility and the average valence of the ion. Thus, it is directly proportional to the net charge resulting from the ionization of the buffering component, i.e., the ratio of the algebraic sum of charged species concentration to the total buffering component concentration in its solution. By the definition provided hereinabove, the electrophoretic reserve capacity of the buffering component will be inversely proportional to its net charge. In other words, the higher the electrophoretic reserve capacity of the buffering component, the lower its net charge, and the lower its net electrophoretic mobility. Taking as an example a simple monovalent weak acid or base, its electrophoretic reserve capacity is 0.50 at its pK. Unlike the buffering capacity, however, the electrophoretic reserve capacity is not symmetrical to either side of the pK. On one side of the pK, the electrophoretic reserve capacity will be about 0.10 at 1 pH unit from the pK, and about 0.01 at 2 pH units from the pK, resulting in high net electrophoretic mobility; whereas, on the other side of the pK, the electrophoretic reserve capacity will be about 0.90 at 1 pH unit from the pK, and about 0.99 at 2 pH units from the pK, resulting in low net electrophoretic mobility. For the purposes of the present invention, an electrophoretic reserve capacity of from at least 0.85 to no more than 0.99 is acceptable, with from at least 0.90 to no more than 0.99 being preferred, and from at least 0.90 to no more than 0.97 being optimal.

The above rules apply to monovalent weak acids or bases. For more complex buffering compounds, such as amino acids and their derivatives and other ampholytes, the concentration of neutral and charged species can be calculated by accepted state of the art procedures (cf, for example, Albert and Serjeant: The Determination of Ionization Constants, Chapman and Hall, 1984). No matter how complex the buffer, the above criteria remain valid: a buffer having a high electrophoretic reserve capacity will have a low electrophoretic net mobility and be a suitable component for a buffer-pair, provided the other component of the pair has a similarly low mobility. Conventional buffers are usually a combination of a weak acid or base with a strong counterion, for example sodium acetate. Such a pair is inherently unsuited for our purpose because of the high net mobility of the sodium ion, always fully charged. It is also important that the buffering pair has sufficient conventional buffering capacity to control the pH. This buffering capacity will be the sum of the net charges of the two buffering components. If their electrophoretic reserve capacity is, for example, 0.95 each, and the total concentration of each component is 100 mMolar, then the buffering is equivalent to the buffering of a 10 mMolar conventional buffer. A buffering concentration of 5 to 10 mMolar is customary in much biochemical work. Thus, it can be seen that the buffers of the present invention have to be utilized at substantially higher concentrations to provide comparable buffering. Usual buffering concentration of these buffers is between 15 and 200 mMolar, the top usable concentration being limited by the solubility of some components. The possibility of using high concentrations while maintaining relatively low electrical conductivity provides an unexpected advantage to our buffering system because a high concentration of amino acids has a general protective effect on proteins and diminishes the tendency of some proteins to precipitate in their isoelectric condition.

The present invention takes advantage of the foregoing concepts to define buffering zones within which each buffering component will exhibit a desirable buffering capacity, combined with high electrophoretic reserve capacity, and low net electrophoretic mobility. Complementary pairs of such buffering components having at least partial overlap of such buffering zones of at least 0.4 pH unit, can then be utilized in order to achieve functionally stable buffering to specific pH values within such buffering zones. Accordingly, in the buffering system of the present invention, each buffering component of the complementary pair has a buffering zone extending no more than 1.25 DH units, and preferably no more than 1 pH unit, within which it exhibits ionization with an electrophoretic reserve capacity within the range of from at least 0.85 to no more than 0.99, and preferably from at least 0.90 to no more than 0.99, and with the bulk of the ionized species being negatively charged for the first buffering component and positively charged for the second buffering component. The overlapping portions of the buffering zones of the two complementary buffering components, covering at least 0.4 pH unit, coincide with and define the narrow buffering zone of the buffering composition, which likewise will extend no more than 1.25 pH units, and preferably no more than 1 pH unit.

A large number of simple buffering components of known chemical composition meeting the above requirements are readily available and suitable for use in the buffering system of the present invention. The first buffering component, exhibiting ionization with the bulk of its ionized species being negatively charged and thus acting as an acidic titrant, may be either a first ampholyte or a weak acid, but there is a better selection of ampholytes than of weak acids. The second buffering component, exhibiting ionization with the bulk of its ionized species being positively charged and thus acting as a basic titrant, may be either a second ampholyte having a higher pI than the first ampholyte, or a weak base. The weak bases are particularly important for higher pH values, as there is a shortage of ampholytes with sufficiently high $pK_1$.

The buffering zones in which the complementary buffering components exhibit their requisite ionization characteristics are determined by the dissociation constants $pK_1$ and $pK_2$ proximal to the pI of the ampholytes and the pK of the weak acid and weak base. The first buffering zone, corresponding to the first buffering component, extends from at least 0.75 pH unit, and preferably at least 1 pH unit, to no more than 2 pH units below the first operative dissociation constant of the first buffering component, i.e., the $pK_2$ of the first ampholyte or the pK of the weak acid. The second buffering zone, corresponding to the second buffering component, extends from at least 0.75 pH unit, and preferably at least 1 pH unit, to no more than 2 pH units above the second operative dissociation constant of the second buffering component, i.e., the $pK_1$ of the second ampholyte or the pK of the weak base. The second operative dissociation constant is at least 2.4 pH units, and preferably from 2.4 to 3.6 pH units, below the first operative dissociation constant, with a difference between the two operative dissociation constants of 3 pH units generally being optimal. Furthermore, when the first buffering component is the first ampholyte, the first buffering zone extends entirely above the pI of the first ampholyte; and when the second buffering component is the second ampholyte, the second buffering zone extends entirely below the pI of the second ampholyte. Since the pI is defined as the midpoint between its proximal $pK_1$ and $pK_2$, the pI will not serve to limit the buffering zone unless the pK spread between the $pK_1$ and $pK_2$ of the ampholyte is 4 or less pH units. In any event, the buffering zone does not include the isoelectric point of either ampholyte. This is in direct contrast to buffering systems previously employed for the generation of pH gradients in IEF, which relied upon the use of ampholytes whose isoelectric points coincide with the desired buffering pH value.

While those ampholytes having a pK spread between their $pK_1$ and $pK_2$ Of less than approximately 3 pH units, were previously considered optimal for the generation of pH gradients in IEF, this is not so with the buffering system of the present invention. To the contrary, ampholytes with a pK spread of 4 or more pH units are preferred for the present invention, even though previously rejected as poor for pH gradient formation. This makes available for pH gradient formation a wide variety of simple ampholytes of known chemical composition, including many of the natural amino acids and their simple derivatives, as well as the so-called Good's buffers.

The narrow buffering zone defined by the overlapping portions of the first and second buffering zones of the complementary first and second buffering components, is at least 0.4 pH unit in order to be of practical value, and can not cover more than 1.25 pH units, and preferably no more than 1 pH unit. Selecting the buffering components so that the second operative dissociation constant is in the range of from 2.4 to 3.6 pH units below the first operative dissociation constant, will ensure the 0.4 pH unit minimum of the narrow buffering zone. The molar ratio in which the two buffering components are employed in formulating the buffering composition, will determine the specific buffering pH value of the composition within the narrow buffering zone. A molar ratio of the second buffering component to the first buffering component within the range of from about 1:9 to about 9:1 will generally be effective for maintaining the buffering pH value within the narrow buffering zone. Within such range of molar ratios, the specific buffering pH value of the composition will increase in a substantially linear relation with the proportion of the second buffering component.

The large selection of ampholytes, weak acids and weak bases, all of known chemical composition, which are suitable for use as buffering components in the buffering system of the present invention, cover a wide range of buffering pH values from about pH 3 to about pH 10. A representative list of suitable complementary buffer pairs and their corresponding pH buffering zones is provided in Table I, below. The pH buffering zones were calculated on the basis of published dissociation constants and cover the range within which the electrophoretic reserve capacity is at least 0.90 but no more than 0.99. This list is provided only by way of example and should not be considered as exhaustive. The characteristic dissociation constants and isoelectric points of the ampholytes listed in Table I are given in Table II, and the characteristic dissociation constants of the weak acids and weak bases in Table I are given in Table III. The dissociation constants of these and other chemicals are listed in various compilations (for instance: Albert and Serjeant, loc. cit.; Jencks and Regenstein: Ionization Constants of Acids and Bases, in Handbook of Biochemistry, 2nd ed., CRC Publishers). It should be also emphasized that the dissociation constants vary somewhat with the presence of other solutes, concentration and temperature, this latter factor being particularly important for dissociation constants in the basic range. Thus, the tabular data provided below should be taken only as approximate and be precised experimentally in a given system.

The abbreviations used in identifying the buffering components in the following tables, in the examples, and in the appended claims, are those conventionally used and well known to those skilled in the art. An alphabetical listing of these abbreviations and their corresponding compounds is provided below.

| Abbreviation | Compound |
|---|---|
| ACES | 2-[(2-amino-2-oxyethyl)-amino] ethanesulfonic acid |
| Ala | alanine |
| AMPSO | 3-[(1,1-dimethyl-2-hydroxyethyl) amino]-2-hydroxypropanesulfonic acid |
| Asn | asparagine |
| Asp | aspartic acid |
| BES | N,N-bis[2-hydroxyethyl]-2-aminoethanesulfonic acid |
| BIS—TRIS | bis[2-hydroxyethyl]imino-tris [hydroxymethyl]-methane |
| CAPSO | 3-[cyclohexylamino]-2-hydroxy-1-propanesulfonic acid |
| DIPSO | 3-[N,N-bis(2-hydroxyethyl)amino]-2-hydroxypropanesulfonic acid |
| EACA | epsilon-aminocaproic acid |
| EPPS | N-[2-hydroxyethyl]-piperazine-N'-[3-propanesulfonic acid] |
| GABA | gamma-aminobutyric acid |
| Gly | glycine |
| HEPES | N-[2-hydroxyethyl]piperazine-N'-[2-ethanesulfonic acid] |
| HEPPSO | N-[2-hydroxyethyl]piperazine-N'-[2-hydroxypropanesulfonic acid] |
| His | histidine |
| MES | 2-[N-morpholino]ethanesulfonic acid |
| MOPS | 3-[N-morpholino]propanesulfonic acid |
| MOPSO | 3-[N-morpholino]-2-hydroxypropanesulfonic acid |
| PIPES | piperazine-N,N'-bis[2-ethanesulfonic acid] |
| POPSO | piperazine-N,N'-bis[2-hydroxypropanesulfonic acid] |
| TAPS | N-tris[hydroxymethyl]methyl-3-aminopropanesulfonic acid |
| TAPSO | 3-[N-tris(hydroxymethyl)methylamino]-2-hydroxypropanesulfonic acid |
| TES | N-tris[hydroxymethyl]methyl-2-aminoethanesulfonic acid |
| TRIS | tris[hydroxymethyl]aminomethane |

TABLE I

| First Buffering Component | Second Buffering Component | PH Buffering Zone Minimum | PH Buffering Zone Maximum |
|---|---|---|---|
| acetic acid | hydroxy proline | 2.92 | 3.76 |
| propionic acid | hydroxy proline | 2.92 | 3.88 |
| propionic acid | serine | 3.12 | 3.88 |
| acetic acid | glutamine | 3.17 | 3.76 |
| propionic acid | glutamine | 3.17 | 3.88 |
| propionic acid | glycine | 3.34 | 3.88 |
| MES | Gly—Gly | 4.15 | 5.10 |
| MES | beta-alanine | 4.60 | 5.10 |
| ACES | beta-alanine | 4.80 | 5.60 |
| ACES | ethyl glutamate | 4.85 | 5.80 |
| MOPSO | ethyl glutamate | 4.85 | 5.85 |
| MOPSO | beta-alanine | 4.90 | 5.60 |
| BES | ethyl glutamate | 5.10 | 5.85 |
| MOPS | ethyl glutamate | 5.20 | 5.85 |
| Gly—Asn | ethyl glutamate | 5.20 | 5.85 |
| ACES | GABA | 5.23 | 5.80 |
| MOPSO | GABA | 5.23 | 5.90 |
| PIPES | GABA | 5.23 | 5.80 |
| BES | GABA | 5.23 | 6.10 |
| Gly—Asn | GABA | 5.23 | 6.20 |
| MOPS | GABA | 5.23 | 6.20 |
| imidazole acetic acid | GABA | 5.35 | 6.23 |
| imidazole acetic acid | EACA | 5.40 | 6.35 |
| ACES | cycloserine | 5.40 | 5.80 |
| BES | cycloserine | 5.40 | 5.90 |
| MOPS | cycloserine | 5.40 | 5.90 |
| MOPSO | cycloserine | 5.40 | 5.90 |
| Gly—Asn | cycloserine | 5.40 | 5.90 |
| imidazole acetic acid | cycloserine | 5.40 | 5.90 |

TABLE I-continued

Complementary Buffer Pairs

| First Buffering Component | Second Buffering Component | PH Buffering Zone Minimum | Maximum |
|---|---|---|---|
| HEPES | EACA | 5.50 | 6.40 |
| TES | EACA | 5.50 | 6.40 |
| HEPES | GABA | 5.50 | 6.23 |
| DIPSO | EACA | 5.60 | 6.40 |
| TAPSO | EACA | 5.60 | 6.40 |
| DIPSO | GABA | 5.60 | 6.23 |
| TAPSO | GABA | 5.60 | 6.23 |
| HEPPSO | aniline | 5.80 | 6.80 |
| DIPSO | creatinine | 5.84 | 6.60 |
| HEPES | creatinine | 5.84 | 6.50 |
| HEPPSO | creatinine | 5.84 | 6.80 |
| POPSO | creatinine | 5.84 | 6.80 |
| TAPSO | creatinine | 5.84 | 6.60 |
| TES | creatinine | 5.84 | 6.50 |
| imidazole acetic acid | creatinine | 5.84 | 6.35 |
| ethyl glutamate | creatinine | 5.85 | 6.84 |
| cycloserine | EACA | 5.90 | 6.40 |
| EPPS | creatinine | 6.00 | 6.84 |
| tri-Gly | creatinine | 6.09 | 6.84 |
| tri-Gly | 8-hydroxyquinoline | 6.09 | 6.91 |
| Ala—Ala | creatinine | 6.14 | 6.84 |
| Ala—Ala | 8-hydroxyquinoline | 6.14 | 6.91 |
| Ala—Gly | 8-hydroxyquinoline | 6.18 | 6.91 |
| Gly—Gly | creatinine | 6.25 | 6.84 |
| TAPS | creatinine | 6.40 | 6.84 |
| TAPS | 8-hydroxyquinoline | 6.40 | 6.91 |
| TAPS | histidine | 7.00 | 7.40 |
| AMPSO | histidine | 7.00 | 7.59 |
| asparagine | histidine | 7.00 | 7.59 |
| AMPSO | beta-picoline | 7.00 | 7.68 |
| glutamine | histidine | 7.13 | 7.56 |
| serine | BIS—TRIS | 7.50 | 8.21 |
| histidine | BIS—TRIS | 7.59 | 8.17 |
| hydroxy proline | BIS—TRIS | 7.66 | 8.50 |
| glycine | BIS—TRIS | 7.66 | 8.50 |
| AMPSO | BIS—TRIS | 7.50 | 8.00 |
| CAPSO | BIS—TRIS | 7.60 | 8.50 |
| CAPSO | diaminopropionic acid | 7.80 | 8.20 |
| glycine | glucosamine | 7.80 | 8.78 |
| alanine | BIS—TRIS | 7.87 | 8.50 |
| GABA | triethanolamine | 8.90 | 9.43 |
| EACA | triethanolamine | 8.90 | 9.80 |
| EACA | TRIS | 9.30 | 9.80 |

TABLE II

| Ampholyte | Ampholytes pK$_1$ | pK$_2$ | pI |
|---|---|---|---|
| ACES | <2 | 6.80 | |
| alanine | 2.35 | 9.87 | 6.11 |
| Ala—Ala | 3.30 | 8.14 | 5.72 |
| Ala—Gly | 3.11 | 8.18 | 5.65 |
| AMPSO | <2 | 9.00 | |
| asparagine | 2.02 | 8.80 | 5.41 |
| BES | <2 | 7.10 | |
| beta-alanine | 3.60 | 10.19 | 6.90 |
| beta-Ala—His | 6.83 | 9.51 | 8.17 |
| CAPSO | <2 | 9.60 | |
| creatinine | 4.84 | 9.20 | 7.02 |
| cycloserine | 4.40 | 7.40 | 5.90 |
| diaminopropionic acid | 6.80 | 9.60 | 8.20 |
| DIPSO | <2 | 7.60 | |
| EACA | 4.40 | 10.80 | 7.60 |
| EPPS | <2 | 8.00 | |
| ethyl glutamate | 3.85 | 7.84 | 5.85 |
| GABA | 4.23 | 10.43 | 7.33 |
| glutamine | 2.17 | 9.13 | 5.65 |
| glycine | 2.35 | 9.78 | 6.07 |
| Gly—Asn | 2.82 | 7.20 | 5.01 |
| Gly—Gly | 3.15 | 8.25 | 5.70 |
| HEPES | <2 | 7.50 | |
| HEPPSO | <2 | 7.80 | |
| histidine | 6.00 | 9.17 | 7.59 |
| hydroxy proline | 1.82 | 9.66 | 5.74 |

TABLE II-continued

| Ampholyte | Ampholytes pK$_1$ | pK$_2$ | pI |
|---|---|---|---|
| 8-hydroxyquinoline | 4.91 | 9.81 | 7.36 |
| imidazole acetic acid | 2.96 | 7.35 | 5.16 |
| MES | <2 | 6.10 | |
| MOPS | <2 | 7.20 | |
| MOPSO | <2 | 6.90 | |
| PIPES | <2 | 6.80 | |
| POPSO | <2 | 7.80 | |
| serine | 2.19 | 9.21 | 5.70 |
| TAPS | <2 | 8.40 | |
| TAPSO | <2 | 7.60 | |
| TES | <2 | 7.50 | |
| tri-Gly | 3.22 | 8.09 | 5.66 |

TABLE III

| Weak Acids and Weak Bases | | |
|---|---|---|
| Weak Acid | Weak Base | pK |
| acetic acid | | 4.76 |
| propionic acid | | 4.88 |
| | aniline | 4.78 |
| | beta-picoline | 5.68 |
| | BIS—TRIS | 6.50 |
| | glucosamine | 6.80 |
| | triethanolamine | 7.90 |
| | TRIS | 8.30 |

By proper selection of the buffer pair of complementary first and second buffering components, the buffering system of the present invention may be utilized to buffer the pH of an aqueous medium to a value within the narrow buffering zone given by the complementary ionization or dissociation characteristics of the buffering components. This buffering zone will cover from 0.4 to 1.25 pH units. To cover any desired pH zone within the range from about pH 3 to about pH 10, the closest matching buffer pair will have to be selected. Such selections may be made, for example, on the basis of the list of complementary buffering pairs listed in Table I or the dissociation constants listed in Tables II and III, following the guidelines set forth herein. Once the selection is made, a solution is formed of the complementary first and second buffering components in the aqueous medium, in appropriate molar ratio and molar concentration effective for buffering the solution to the desired pH value. In general, the sum of the molar concentrations of the first and second buffering components in the solution should be within the range of from about 30 to 300 mMolar. In the resulting buffer solution, the overlapping portions of the first and second buffering zones will buffer the solution to a value within such narrow buffering zone. The specific buffering pH value of the buffer solution within the narrow buffering zone, will be determined by the molar ratio of the two buffering components in the buffer solution.

The buffered aqueous medium may optionally have incorporated therein a water-miscible organic solvent, such as a lower alkanol, e.g., methanol or ethanol, or any one or more of the additives commonly incorporated in electrophoretic buffer solutions for facilitating use thereof in isoelectric focusing and other electrophoretic processes. Such additives include, for example, hydrophilic gelling agents, such as polyacrylamide or agarose; viscosity enhancers, such as glycerol, sucrose, or a variety of hydrophilic polymeric derivatives, such as hydroxypropyl methycellulose; detergents, such as known under the tradenames of "Chaps", "Chapso", "Triton X-100" "Tween 20", "Brij", etc.; protein solubilizing agents, such as urea; affinity ligands, such as various lectins; and reducing agents, such as mercaptoethanol or dithiothreitol.

The new buffering system is suitable for use in many biological applications, such as various forms of liquid chromatography, enzyme assays and reactions, tissue culture, etc. There is a shortage of buffers suitable for biological applications, phosphate and bicarbonate buffers being most widely used. The present invention provides the means for buffering with biologically acceptable chemicals, mostly amino acids and simple derivatives, Good's buffers and some weak bases and weak acids, all readily available in commerce.

It is most likely that the new buffers will find their greatest usefulness in electrophoresis, because of their low net electrophoretic mobility. The new buffers can be used in a variety of ways, depending on the apparatus in which the buffers will be used and the purpose of the separation.

A first preferred method of usage of the complementary buffer pair of the present invention is to use the first and second buffering components in a substantially constant molar ratio in order to formulate a stable substantially uniform pH in any apparatus for electrophoresis or isoelectric focusing. One may, for instance, utilize a continuous flow electrophoresis apparatus (for example, Hannig and Wirth, U.S. Pat. No. 4,061,560), a rotating isoelectric focusing apparatus (Bier, U.S. Pat. No. 4,588,492) or a recycling focusing instrument (Bier, U.S. Pat. No. 4,362,612; Bier and Twitty, U.S. Pat. No. 4,897,169). In the latter case, it would represent a modification of the process of using a simple ampholyte, described by Bier and Long (J. Chromatogr. Vol. 604, pp.73–83, 1992). It would have the great advantage of not being limited in the selection of operational pH values to the actual isoelectric point of specific ampholytes, but would provide great flexibility in the choice of operational pH value. As described by Bier and Long, in such applications the pH of the buffer does not remain perfectly constant and flat across the width of the focusing chamber, but will slowly develop a mild slope, lower at the anode, higher at the cathode, due to the low residual mobility of the buffering components.

An alternate usage of the buffer compositions of the present invention, particularly for isoelectric focusing, is to precast a desired pH gradient over the narrow pH zone obtainable with a single complementary buffer pair. Such pH gradients can be readily formed by progressively varying the molar ratio of the two components over the calculated proportions of first and second buffer components. The pH gradient can be a substantially continuous one, formed by a smoothly varying molar ratio of the two components, or can be a step DH gradient, obtained by preparing a set of buffer solutions, each having the same complementary pair of first and second buffering components, but in different molar ratios to correspond to different specific buffering pH values progressively increasing from the lower limit to the upper limit of the desired narrow buffering zone. Other means of forming pH gradients will be obvious to anyone skilled in the art.

The above-described modes of utilizing the buffering system of the present invention are illustrated by the following examples.

EXAMPLE 1

The experiment of this example had at its objective the confirmation of pH values and electrophoretic stability of buffer systems as per the concepts of this invention. The complementary buffer pair chosen had as the first buffering component a Good's buffer known as MOPS, and as the second buffering component the gamma-aminobutyric acid, abbreviated as GABA. The operative dissociation constants are for MOPS, $pK_2=7.20$ and for GABA, $pK_1=4.23$, as per Table II.

Figure 1:
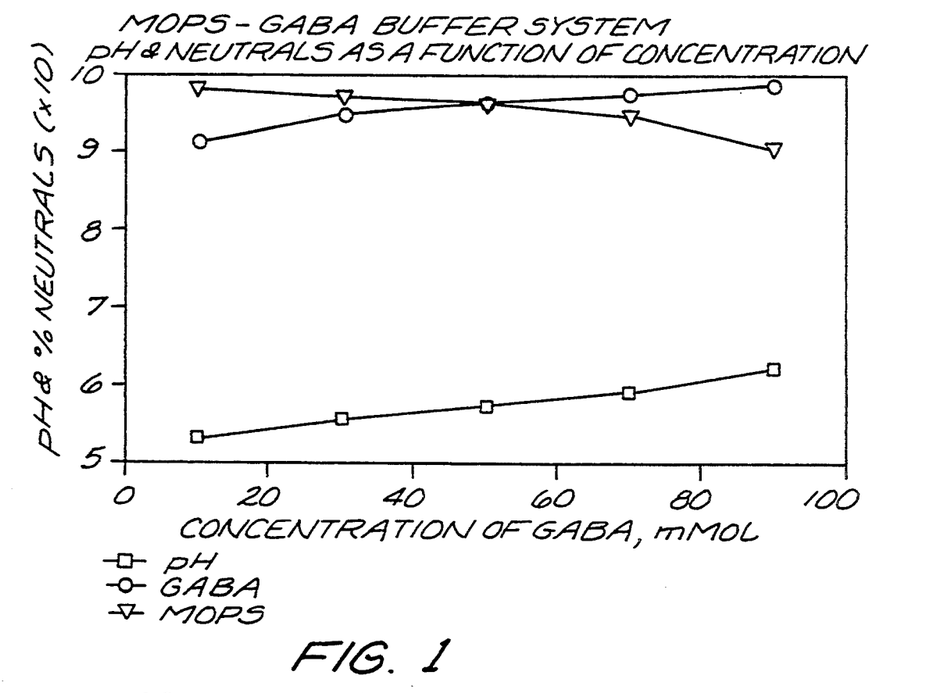
FIGS. 1, 2 and 3 are graphs showing pH and concentration profiles of two different buffering compositions in accordance with the present invention.

The concentrations of the two ampholytes were made to vary from 90 mMMOPS/10 mM GABA to 10 mMMOPS/90 mMGABA. In FIG. 1 are shown the computer-predicted profiles for pH values and the concentrations of the neutral species of the two ampholytes, as a function of GABA concentration. The graphs show that the pH is expected to increase nearly linearly over this concentration range, remaining within the narrow zone of about 1 pH unit. The concentration of neutral species is above 90% over the whole range, thus giving the desired high electrophoretic reserve capacity.

A 50/50 mMMOPS-GABA buffer was selected for the confirming focusing experiment. For focusing, the commercially available "Miniphor" isoelectric focusing apparatus was used. This patented apparatus (Bier and Twitty, U.S. Pat. No. 4,897,169, issued Jan. 30, 1990) is produced by Protein Technologies, Inc., Tucson, Ariz. and distributed by Rainin Instrument Co., Inc., Woburn, Me. It utilizes the principle of recycling isoelectric focusing for protein separations. The apparatus was loaded with approximately 35 ml. of the MOPS-GABA buffer, and exposed to an applied voltage of 750 volts for the first 45 min., followed by 15 min. of 500 volts, while the recycling of the buffer was continued throughout. This protocol is customarily used for protein separations. The focusing temperature was maintained at about 10° C. At the end of the focusing a total of 20 fractions was collected, these fractions representing the whole contents, electrode-to-electrode, of the apparatus.

Figure 2:
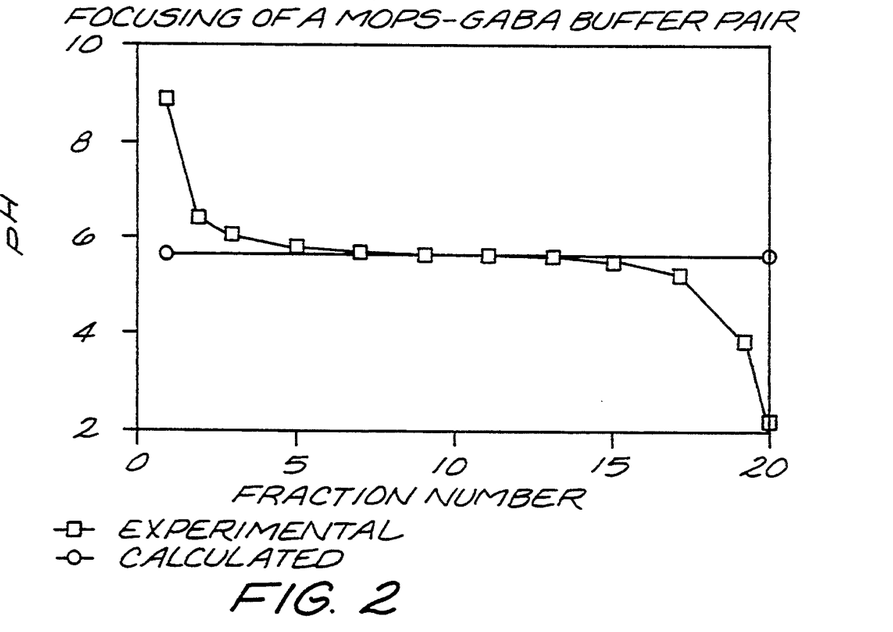

FIG. 2 compares the experimental pH profile of the 20 fractions with the projected pH for the 50/50 mMMOPS-GABA buffer, shown as the horizontal line across the plot. It can be seen that there is excellent correspondence of the experimental and predicted pH values through the central fractions, but deviation from those values at both ends of the apparatus. This is normal, as it is the result of ion polarization close to the membranes separating the focusing chamber from the electrodes compartments. In fact, the focusing process is supposed to increase the pH at the cathode and decrease at the anode. Had there been any protein in the buffer system with the appropriate pI it would have focused to the center compartments, the more basic and acidic components migrating to the respective ends of the chamber. This, of course, is the intended purpose of such an operation. Moreover, any ion impurities in the system, such as sodium chloride that may be present in the protein sample, will accumulate in these fractions.

EXAMPLE 2

This example, in fact, is a sequence of 24 focusing runs carried out to test the effective pH range of eight complementary buffer pairs, each pair having been used at three concentration ratios. The protocol of Example 1 was used, except that 0.4% of "Methocel E4M Prem" was used as a viscosity enhancer. "Methocel E4M" is a Dow Chemical Co. brand of hydroxypropyl methylcellulose. Table IV lists the experimental pH values obtained for each buffer pair in the "Miniphor" apparatus.

Each buffer pair was tested at 3 concentrations: 80/20 mM, 50/50 mM, and 20/80 mM ratios of first to second component. The data are the pH values recorded for the center fraction 11 of the 20 fractions collected in each focusing run. A comparison of these data with the projected pH buffering zones of Table I shows the approximate validity of the theoretical projections over a wide range of pH values. A closer examination of the data shows that the zones of pH values are skewed to a little bit higher values than predicted. This is the consequence of temperature effects on the dissociation constants. The literature data for pK values cited in Tables II and III and used for Table I are reported for room temperature. Our runs were all made at approximately 10° C., needing a correction. This will be exemplified with data of Example 3.

TABLE IV

Experimental pH Values on Selected Buffer Pairs

| BUFFERING COMPONENTS | | pH VALUE DATA | | |
|---|---|---|---|---|
| FIRST | SECOND | 80/20 | 50/50 | 20/80 |
| MES | Gly—Gly | 4.35 | 4.82 | 5.12 |
| ACES | beta-alanine | 5.01 | 5.42 | 5.70 |
| MOPS | GABA | 5.41 | 5.74 | 6.04 |
| TAPSO | EACA | 5.92 | 6.22 | 6.50 |
| EPPS | creatinine | 6.14 | 6.60 | 6.91 |
| AMPSO | BIS—TRIS | 7.86 | 8.16 | 8.50 |
| CAPSO | BIS—TRIS | 8.22 | 8.57 | 8.83 |
| EACA | triethanolamine | 9.45 | 9.74 | 10.00 |

TABLE IV

Experimental pH Values on Selected Buffer Pairs

| BUFFERING COMPONENTS | | pH VALUE DATA | | |
|---|---|---|---|---|
| FIRST | SECOND | 80/20 | 50/50 | 20/80 |
| MES | Gly—Gly | 4.35 | 4.82 | 5.12 |
| ACES | beta-alanine | 5.01 | 5.42 | 5.70 |
| MOPS | GABA | 5.41 | 5.74 | 6.04 |
| TAPSO | EACA | 5.92 | 6.22 | 6.50 |
| EPPS | creatinine | 6.14 | 6.60 | 6.91 |
| AMPSO | BIS—TRIS | 7.86 | 8.16 | 8.50 |
| CAPSO | BIS—TRIS | 8.22 | 8.57 | 8.83 |
| EACA | triethanolamine | 9.45 | 9.74 | 10.00 |

EXAMPLE 3

The experiment of this example was carried out to test the applicability of the new buffers in an isoelectric focusing apparatus of different design than that used in Examples 1 and 2. The apparatus used is also based on recycling isoelectric focusing, as patented by Bier (U.S. Pat. No. 4,362,612, issued Dec. 7, 1982). This is a modular apparatus, the focusing chamber comprising an arbitrary number of subcompartments, separated from each other by ion non-selective permeable membranes, in fact monofilament screens. These serve to streamline the flow of process fluid within the focusing chamber. A 5-compartment apparatus was utilized, with an effective membrane cross-section of 10 cm sq. The AMPSO-His buffer system was chosen, as it was expected that it covers a pH zone suitable for focusing of human hemoglobin, with an isoelectric point distribution of about pH 7.2 to 7.6. Five solutions were individually prepared, with concentrations of 90/10, 70/30, 50/50, 30/70, and 10/90 mMolar AMPSO/His buffer. Each apparatus subcompartment was filled individually with the respective buffer, taking care to minimize cross-contamination. In addition, 40 mg of a recombinant human hemoglobin, was added uniformly to the buffers. An electric field of 400 volts was applied for one hour, following which the contents of the five compartments were collected.

Gel electrophoresis has shown that the hemoglobin protein has mainly focused to the center compartment, the 50/50 compartment, with lesser concentrations in the first two subcompartments. The last two compartments were essentially protein-free. The hemoglobin sample consisted of three subfractions, with close distribution of isoelectric points. Visual inspection has shown that there was a partitioning of the hemoglobin fractions between the subcompartments, but this was not quantified.

Figure 3:
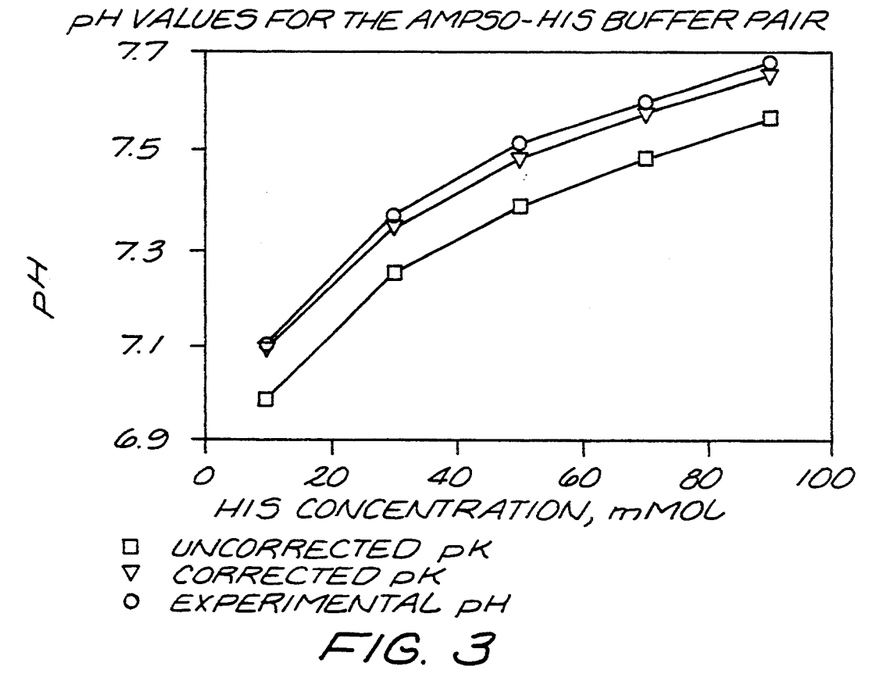

FIG. 3 shows the originally calculated pH profile for the five buffer concentrations and the experimental pH profile. It can be readily seen that the experimental data were offset by about 0.1–0.2 pH units to higher pH values than calculated. A much better fit was obtained by recalculating the pH profiles using corrected $PK_2$ values of both, AMPSO and His. The corresponding data are shown below in Table V and in the graph of FIG. 3. The rationale for the higher $PK_2$ values is the temperature difference between the published and the experimental data. Unfortunately, accurate data for all temperature ranges are not available and, thus, this factor introduces a certain element of uncertainty in prediction of the pH values. This applies more to data in basic media than in acidic media.

TABLE V pH Values for the AMPSO—HIS Buffer Pair Using Literature and Corrected pK Values

| BUFFER CONCENTRATIONS | | | | | |
|---|---|---|---|---|---|
| AMPSO, mM | 90 | 70 | 50 | 30 | 10 |
| His. mM | 10 | 30 | 50 | 70 | 90 |
| CORRESPONDING pH VALUES | | | | | |
| uncorrected pK | 6.99 | 7.26 | 7.39 | 7.48 | 7.56 |
| experimental pH | 7.10 | 7.37 | 7.51 | 7.59 | 7.67 |
| corrected pK | 7.09 | 7.35 | 7.48 | 7.57 | 7.64 |
| DISSOCIATION CONSTANTS | | | | | |
| | $pK_1$ | | $pK_2$ | | |
| AMPSO, literature | <2 | | 9.00 | | |
| AMPSO, corrected | <2 | | 9.20 | | |
| His, literature | 6.00 | | 9.17 | | |
| His, corrected | 6.00 | | 9.34 | | |

What is claimed is:

1. A buffering composition capable of buffering an aqueous medium to a pH value within a narrow buffering zone covering from 0.4 to 1.25 pH units in a range of from about pH 3 to about pH 10, said composition consisting essentially of a buffer pair of first and second buffering components exhibiting complementary ionization characteristics providing said buffer pair with low net electrophoretic mobility within said narrow buffering zone;

said first buffering component having a first operative dissociation constant which establishes a first buffering zone extending below said first operative dissociation constant and within which said first buffering component exhibits ionization with an electrophoretic reserve capacity within the range of from at least 0.85 to no more than 0.99 and with the bulk of its ionized species being negatively charged;

said second buffering component having a second operative dissociation constant which is at least 2.4 pH units below said first operative dissociation constant and which establishes a second buffering zone extending above said second operative dissociation constant and within which said second buffering component exhibits ionization with an electrophoretic reserve capacity within the range of from at least 0.85 to no more than 0.99 and with the bulk of its ionized species being positively charged; said first and second buffering zones having overlapping portions covering from 0.4 to 1.25 pH units, said overlapping portions coinciding with and defining said narrow buffering zone, the molar ratio of said second buffering component to said first buffering component being within a range effective for maintaining the buffering pH value within said narrow buffering zone, with the proviso that said buffer pair is not a combination of a first ampholyte whose $pK_2$ is 8.0 and a second ampholyte whose $pK_1$ is 5.0, and with the further proviso that said buffer pair is not alpha-Asp-His/isoglutamine.

2. The buffering composition of claim 1, wherein said electrophoretic reserve capacities are each within the range of from at least 0.90 to no more than 0.99, and said first and second buffering zones and said narrow buffering zone each cover no more than 1 pH unit.

3. The buffering composition of claim 2, wherein said electrophoretic reserve capacities are each within the range of from at least 0.90 to no more than 0.97.

4. The buffering composition of claim 1, wherein said first buffering zone extends from at least 0.75 to no more than 2 pH units below said first operative dissociation constant, and said second buffering zone extends from at least 0.75 to no more than 2 pH units above said second operative dissociation constant.

5. The buffering composition of claim 4, wherein said first buffering zone extends from at least 1 to no more than 2 pH units below said first operative dissociation constant, and said second buffering zone extends from at least 1 to no more than 2 pH units above said second operative dissociation constant.

6. The buffering composition of claim 1, wherein said first buffering component is selected from the group consisting of a first ampholyte and a weak acid, said first ampholyte having an isoelectric point pI and dissociation constants $pK_1$ and $pK_2$ proximal to the pI, said weak acid having a dissociation constant pK, said first operative dissociation constant being the $pK_2$ of said first ampholyte or the pK of said weak acid; and said second buffering component is selected from the group consisting of a second ampholyte and a weak base, said second ampholyte having an isoelectric point pI and dissociation constants $pK_1$ and $pK_2$ proximal to the pI, the pI of said second ampholyte being higher than that of said first ampholyte, said weak base having a dissociation constant pK, said second operative dissociation constant being the $pK_1$ of said second ampholyte or the pK of said weak base.

7. The buffering composition of claim 6, wherein at least one of said first and second buffering components is an ampholyte; when said first buffering component is said first ampholyte, said first buffering zone extends entirely above the pI of said first ampholyte; and when said second buffering component is said second ampholyte, said second buffering zone extends entirely below the pI of said second ampholyte.

8. The buffering composition of claim 7, wherein each of said first and second ampholytes has a pK spread between its $pK_1$ and $pK_2$ of at least 4 pH units.

9. The buffering composition of claim 7, wherein said first buffering component is said first ampholyte, and said second buffering component is said second ampholyte.

10. The buffering composition of claim 7, wherein said first buffering component is said first ampholyte, and said second buffering component is said weak base.

11. The buffering composition of claim 1, wherein said narrow buffering zone is in a range of from about pH 3 to about pH 7, and said buffer pair is selected from the group consisting of propionic acid/serine, MES/Gly-Gly, MES/beta-alanine, ACES/beta-alanine, MOPSO/beta-alanine, ACES/GABA, MOPSO/GABA, PIPES/GABA, BES/GABA, MOPS/GABA, HEPES/EACA, TES/EACA, DIPSO/EACA, TAPSO/EACA, DIPSO/GABA, TAPSO/GABA, DIPSO/creatinine, HEPES/creatinine, HEPPSO/creatinine, POPSO/creatinine, TAPSO/creatinine and TES/creatinine.

12. The buffering composition of claim 1, wherein said narrow buffering zone is in a range of from about pH 7 to about pH 10, and said buffer pair is selected from the group consisting of TAPS/histidine, AMPSO/histidine, asparagine/histidine, AMPSO/beta-picoline, glutamine/histidine, serine/BIS-TRIS, histidine/BIS-TRIS, hydroxy proline/BIS-TRIS, glycine/BIS-TRIS, AMPSO/BIS-TRIS, CAPSO/BIS-TRIS, CAPSO/diaminopropionic acid, 8 glycine/glucosamine, alanine/BIS-TRIS, GABA/triethanolamine, EACA/triethanolamine and EACA/TRIS.

13. The buffering composition of claim 1, wherein said second operative dissociation constant is from 2.4 to 3.6 pH units below said first operative dissociation constant.

14. The buffering composition of claim 1, wherein said molar ratio is within the range of from about 1:9 to about 9:1.

15. The buffering composition of claim 14, wherein said molar ratio is selected to correspond to a preselected specific buffering pH value within said narrow buffering zone.

16. A buffered medium comprising the buffering composition of claim 1, dissolved in an aqueous medium in a molar concentration of said first and second buffering components effective for buffering said medium to a pH value within said narrow buffering zone.

17. The buffered medium of claim 16, wherein the sum of the molar concentrations of said first and second buffering components is within the range of from about 30 mMolar to about 300 mMolar.

18. The buffered medium of claim 16, further including at least one additive for facilitating use of said buffered medium in an electrophoretic process, said additive being selected from the group consisting of a hydrophilic gelling agent, a viscosity enhancer, a detergent, urea, an affinity ligand and a reducing agent.

19. A method of buffering an aqueous medium to a pH value within a narrow buffering zone covering from 0.4 to 1.25 pH units in a range of from about pH 3 to about pH 10, said method comprising forming a solution in said aqueous medium of a buffering composition consisting essentially of a buffer pair of first and second buffering components, the selection criteria for said first and second buffering components being complementary ionization characteristics providing said buffer pair with low net electrophoretic mobility within said narrow buffering zone;

said first buffering component being selected so as to have a first operative dissociation constant which establishes a first buffering zone extending below said first operative dissociation constant and within which said first buffering component exhibits ionization with an electrophoretic reserve capacity within the range of from at least 0.85 to no more than 0.99 and with the bulk of its ionized species being negatively charged;

said second buffering component being selected so as to have a second operative dissociation constant which is at least 2.4 pH units below said first operative dissociation constant and which establishes a second buffering zone extending above said second operative dissociation constant and within which said second buffering component exhibits ionization with an electrophoretic reserve capacity within the range of from at least 0.85 to no more than 0.99 and with the bulk of its ionized species being positively charged;

said first and second buffering components being further selected so that said first and second buffering zones have overlapping portions covering from 0.4 to 1.25 pH units, said overlapping portions coinciding with and defining said narrow buffering zone, the molar ratio of said second buffering component to said first buffering component and the sum of the molar concentrations of said first and second buffering components in said medium being effective for buffering said medium to said pH value.

20. The method of claim 19, wherein said electrophoretic reserve capacities are each within the range of from at least 0.90 to no more than 0.99, and said first and second buffering zones and said narrow buffering zone each cover no more than 1 pH unit.

21. The method of claim 20, wherein said electrophoretic reserve capacities are each within the range of from at least 0.90 to no more than 0.97.

22. The method of claim 19, wherein said first buffering zone extends from at least 0.75 to no more than 2 pH units below said first operative dissociation constant, and said second buffering zone extends from at least 0.75 to no more than 2 pH units above said second operative dissociation constant.

23. The method of claim 22, wherein said first buffering zone extends from at least 1 to no more than 2 pH units below said first operative dissociation constant, and said second buffering zone extends from at least 1 to no more than 2 pH units above said second operative dissociation constant.

24. The method of claim 19, wherein said first buffering component is selected from the group consisting of a first ampholyte and a weak acid, said first ampholyte having an isoelectric point pI and dissociation constants $pK_1$ and $PK_2$ proximal to the pI, said weak acid having a dissociation constant pK, said first operative dissociation constant being the $pK_2$ of said first ampholyte or the pK of said weak acid; and said second buffering component is selected from the group consisting of a second ampholyte and a weak base, said second ampholyte having an isoelectric point pI and dissociation constants $pK_1$ and $pK_2$ proximal to the pI, the pI of said second ampholyte being higher than that of said first ampholyte, said weak base having a dissociation constant pK, said second operative dissociation constant being the $pK_1$ of said second ampholyte or the pK of said weak base.

25. The method of claim 24, wherein at least one of said first and second buffering components is an ampholyte; when said first buffering component is said first ampholyte, said first buffering zone extends entirely above the pI of said first ampholyte; and when said second buffering component is said second ampholyte, said second buffering zone extends entirely below the pI of said second ampholyte.

26. The method of claim 25, wherein each of said first and second ampholytes has a pK spread between its $pK_1$ and $pK_2$ of at least 4 pH units.

27. The method of claim 25, wherein said first buffering component is said first ampholyte, and said second buffering component is said second ampholyte.

28. The method of claim 25, wherein said first buffering component is said first ampholyte, and said second buffering component is said weak base.

29. The method of claim 19, wherein said narrow buffering zone is in a range of from about pH 3 to about pH 7, and said buffer pair is selected from the group consisting of propionic acid/serine, MES/Gly-Gly, MES/beta-alanine, ACES/beta-alanine, MOPSO/beta-alanine, ACES/GABA, MOPSO/GABA, PIPES/GABA, BES/GABA, MOPS/GABA, HEPES/EACA, TES/EACA, DIPSO/EACA, TAPSO/EACA, DIPSO/GABA, TAPSO/GABA, DIPSO/creatinine, HEPES/creatinine, HEPPSO/creatinine, POPSO/creatinine, TAPSO/creatinine and TES/creatinine.

30. The method of claim 19, wherein said narrow buffering zone is in a range of from about pH 7 to about pH 10, and said buffer pair is selected from the group consisting of TAPS/histidine, AMPSO/histidine, asparagine/histidine, AMPSO/beta-picoline, glutamine/histidine, serine/BIS-TRIS, histidine/BIS-TRIS, hydroxy proline/BIS-TRIS, glycine/BIS-TRIS, AMPSO/BIS-TRIS, CAPSO/BIS-TRIS, CAPSO/diaminopropionic acid, glycine/glucosamine, alanine/BIS-TRIS, GABA/triethanolamine, EACA/triethanolamine and EACA/TRIS.

31. The method of claim 19, wherein said second operative dissociation constant is from 2.4 to 3.6 pH units below said first operative dissociation constant.

32. The method of claim 19, wherein said molar ratio is within the range of from about 1:9 to about 9:1.

33. The method of claim 32, wherein said molar ratio is selected to correspond to a preselected specific buffering pH value within said narrow buffering zone.

34. The method of claim 19, wherein said sum of the molar concentrations is within the range of from about 30 mMolar to about 300 mMolar.

35. In a method of electrophoretically separating of a mixture of biological materials comprising the steps of applying a d.c. electric field to a solution or suspension of said mixture in an aqueous medium having a controlled pH, and allowing said materials to separatively migrate within said medium under the influence of said applied electric field, the improvement comprising controlling the pH of said medium with a buffering composition having a narrow buffering zone covering from 0.4 to 1.25 pH units in a range of from about pH 3 to about pH 10, said composition consisting essentially of a buffer pair of first and second buffering components exhibiting complementary ionization characteristics providing said buffer pair with low net electrophoretic mobility within said narrow buffering zone;

said first buffering component having a first operative dissociation constant which establishes a first buffering zone extending below said first operative dissociation constant and within which said first buffering component exhibits ionization with an electrophoretic reserve capacity within the range of from at least 0.85 to no more than 0.99 and with the bulk of its ionized species being negatively charged;

said second buffering component having a second operative dissociation constant which is at least 2.4 pH units below said first operative dissociation constant and which establishes a second buffering zone extending above said second operative dissociation constant and within which said second buffering component exhibits ionization with an electrophoretic reserve capacity within the range of from at least 0.85 to no more than 0.99 and with the bulk of its ionized species being positively charged;

said first and second buffering zones having overlapping portions covering from 0.4 to 1.25 pH units, said overlapping portions coinciding with and defining said narrow buffering zone, the molar ratio of said second buffering component to said first buffering component being within a range effective for maintaining the buffering pH value within said narrow buffering zone.

36. The method of claim 35, wherein the pH of said medium is buffered to a substantially uniform pH by said molar ratio being substantially constant throughout said medium.

37. The method of claim 35, wherein the pH of said medium is buffered so as to form a narrow pH gradient of from 0.4 to 1.25 pH units by said molar ratio being progressively varied within said medium in substantially continuous or step-wise increments, and said electrophoretic separation of said materials is effected by isoelectric focusing.

38. The method of claim 35, wherein said electrophoretic reserve capacities are each within the range of from at least 0.90 to no more than 0.99, and said first and second buffering zones and said narrow buffering zone each cover no more than 1 pH unit.

39. The method of claim 38, wherein said electrophoretic reserve capacities are each within the range of from at least 0.90 to no more than 0.97.

40. The method of claim 35, wherein said first buffering zone extends from at least 0.75 to no more than 2 pH units below said first operative dissociation constant, and said second buffering zone extends from at least 0.75 to no more than 2 pH units above said second operative dissociation constant.

41. The method of claim 40, wherein said first buffering zone extends from at least 1 to no more than 2 pH units below said first operative dissociation constant, and said second buffering zone extends from at least 1 to no more than 2 pH units above said second operative dissociation constant.

42. The method of claim 35, wherein said first buffering component is selected from the group consisting of a first ampholyte and a weak acid, said first ampholyte having an isoelectric point pI and dissociation constants $pK_1$ and $pK_2$ proximal to the pI, said weak acid having a dissociation constant pK, said first operative dissociation constant being the $pK_2$ of said first ampholyte or the pK of said weak acid; and said second buffering component is selected from the group consisting of a second ampholyte and a weak base, said second ampholyte having an isoelectric point pI and dissociation constants $pK_1$ and $pK_2$ proximal to the pI, the pI of said second ampholyte being higher than that of said first ampholyte, said weak base having a dissociation constant pK, said second operative dissociation constant being the $pK_1$ of said second ampholyte or the pK of said weak base.

43. The method of claim 42, wherein at least one of said first and second buffering components is an ampholyte; when said first buffering component is said first ampholyte, said first buffering zone extends entirely above the pI of said first ampholyte; and when said second buffering component is said second ampholyte, said second buffering zone extends entirely below the pI of said second ampholyte.

44. The method of claim 43, wherein each of said first and second ampholytes has a pK spread between its $pK_1$ and $pK_2$ of at least 4 pH units.

45. The method of claim 43, wherein said first buffering component is said first ampholyte, and said second buffering component is said second ampholyte.

46. The method of claim 43, wherein said first buffering component is said first ampholyte, and said second buffering component is said weak base.

47. The method of claim 35, wherein said narrow buffering zone is in a range of from about pH 3 to about pH 7, and said buffer pair is selected from the group consisting of propionic acid/serine, MES/Gly-Gly, MES/beta-alanine, ACES/beta-alanine, MOPSO/beta-alanine, ACES/GABA, MOPSO/GABA, PIPES/GABA, BES/GABA, MOPS/GABA, HEPES/EACA, TES/EACA, DIPSO/EACA, TAPSO/EACA, DIPSO/GABA, TAPSO/GABA, DIPSO/creatinine, HEPES/creatinine, HEPPSO/creatinine, POPSO/creatinine, TAPSO/creatinine and TES/creatinine.

48. The method of claim 35, wherein said narrow buffering zone is in a range of from about pH 7 to about pH 10, and said buffer pair is selected from the group consisting of TAPS/histidine, AMPSO/histidine, asparagine/histidine, AMPSO/beta-picoline, glutamine/histidine, serine/BIS-TRIS, histidine/BIS-TRIS, hydroxy proline/BIS-TRIS, glycine/BIS-TRIS, AMPSO/BIS-TRIS, CAPSO/BIS-TRIS, CAPSO/diaminopropionic acid, glycine/glucosamine, alanine/BIS-TRIS, GABA/triethanolamine, EACA/triethanolamine and EACA/TRIS.

49. The method of claim 35, wherein said second operative dissociation constant is from 2.4 to 3.6 pH units below said first operative dissociation constant.

50. The method of claim 35, wherein said molar ratio is within the range of from about 1:9 to about 9:1.

51. The method of claim 35, wherein the sum of the molar concentrations of said first and second buffering components in said medium is within the range of from about 30 mMolar to about 300 mMolar.

52. The method of claim 35, wherein said medium includes at least one additive for facilitating said electrophoretic separation, said additive being selected from the group consisting of a hydrophilic gelling agent, a viscosity enhancer, a detergent, urea, an affinity ligand and a reducing agent.

* * * * *